(12) United States Patent
Dent

(10) Patent No.: US 7,984,663 B2
(45) Date of Patent: Jul. 26, 2011

(54) ROBOT HEAD COMPRISING SPINDLE DRIVE

(75) Inventor: Alastair Dent, Oxford (GB)

(73) Assignee: The Acrobot Company Limited, London (GB)

( * ) Notice: Subject to any disclaimer, the term of this patent is extended or adjusted under 35 U.S.C. 154(b) by 784 days.

(21) Appl. No.: 10/526,258

(22) PCT Filed: Aug. 1, 2003

(86) PCT No.: PCT/GB03/03354
§ 371 (c)(1),
(2), (4) Date: Sep. 12, 2005

(87) PCT Pub. No.: WO2004/021909
PCT Pub. Date: Mar. 18, 2004

(65) Prior Publication Data
US 2006/0182596 A1 Aug. 17, 2006

(30) Foreign Application Priority Data
Sep. 3, 2002 (GB) .................................. 0220460.0

(51) Int. Cl.
*B25J 17/00* (2006.01)

(52) U.S. Cl. ......... 74/490.03; 74/490.11; 901/9; 901/23
(58) Field of Classification Search ............... 901/9, 23, 901/24; 74/25, 89, 89.23, 89.34, 99 R, 490.01, 74/490.03, 490.07, 490.11, 490.12
See application file for complete search history.

(56) References Cited

U.S. PATENT DOCUMENTS

| 4,430,037 | A | | 2/1984 | Bisiach | |
| 4,565,104 | A | * | 1/1986 | Akin | 74/89.23 |
| 4,825,714 | A | * | 5/1989 | Yamanaka et al. | 74/89.23 |
| 6,494,005 | B2 | * | 12/2002 | Zimmerman | 52/296 |
| 2002/0120254 | A1 | | 8/2002 | Julian et al. | |
| 2003/0109953 | A1 | * | 6/2003 | Zufle | 700/204 |
| 2003/0144649 | A1 | * | 7/2003 | Ghodoussi et al. | 606/1 |

FOREIGN PATENT DOCUMENTS
EP 0 927 612 A1 7/1999
(Continued)

OTHER PUBLICATIONS
Search Report for GB 0220460.0 dated Feb. 18, 2003.
(Continued)

*Primary Examiner* — Thomas R. Hannon
*Assistant Examiner* — James Pilkington
(74) *Attorney, Agent, or Firm* — Ungaretti & Harris LLP

(57) ABSTRACT

A robot head, for example for use in surgery, provides a back-drivable system allowing a surgeon to closely control the position of a cutter or other tool. The cutter is mounted at the end of a telescopic arm (20) which can be rotated about two independent perpendicular axes. Rotation about each axis is controlled by a separate motor (30') which turns a lead screw (32). A bearing (34) travels along the lead screw and changes the angle of an offset crank (36) to cause the required rotation about the axis. The current rotational position about each axis is determined by a sensor at the output. A second sensor independently determines the position of the corresponding motor (30) and the two measured positions are compared. If they differ, the power to the cutter is immediately switched off.

14 Claims, 7 Drawing Sheets

FOREIGN PATENT DOCUMENTS

| | | |
|---|---|---|
| JP | 3281191 | 12/1991 |
| JP | 4183593 | 6/1992 |
| JP | 4244388 | 9/1992 |
| JP | 9073873 | 3/1997 |
| JP | 200316872 | 11/2000 |
| WO | WO 97/00649 | 1/1997 |
| WO | WO 02/060653 A2 | 8/2002 |

OTHER PUBLICATIONS

International Search Report for PCT/GB03/03354 mailed Feb. 6, 2004.

* cited by examiner

ROBOT HEAD COMPRISING SPINDLE DRIVE

CROSS-REFERENCE TO RELATED APPLICATIONS

This Application is a U.S. National filing under §371 of International Application No. PCT/GB2003/003354, with an international filing date of Aug. 1, 2003, now pending, claiming priority from Great Britain Application No. GB2002/20460.0, with a filing date of Sep. 3, 2002, now pending, and herein incorporated by reference.

TECHNICAL FIELD

The present invention relates to robot heads and particularly, although not exclusively, to a head for a surgical robot.

BACKGROUND OF THE INVENTION

In one type of robotically-assisted surgical procedure, a cutting implement (for example to cut bone) is mounted on an adjustable robot head which is itself held in position by a static gross-positioning device. The robot head has a manually-graspable handle which allows the surgeon to move the cutter. Typically, the cutter may be mounted at the end of a telescopic arm, and by applying force to the handle the surgeon may cause the arm to extend and/or to rotate about mutually-perpendicular pitch and yaw axes. Motors within the head respond to forces applied to the handle to ensure that the cutter moves smoothly to the position the surgeon requires. The head may include constraint mechanisms, implemented either in hardware or in software, which prevent the surgeon from moving the cutter into regions which have previously been defined as unsafe. Force feedback mechanisms may also be provided so that the surgeon receives tactile force feedback through the handle.

Of particular importance in surgical applications—although it may be of importance in other applications as well—is the precision with which the cutter can be positioned by the surgeon. Current systems are somewhat limited in this respect, because of relatively high friction in the mechanical components, along with a certain amount of "play" or backlash. A further requirement of course is safety, and concerns have been expressed as to the potentially serious injuries that could be caused to a patient in the event of a mechanical failure of a traditional robot head, or a failure in the control system or its software.

SUMMARY OF THE INVENTION

It is an object of the present invention at least to alleviate these perceived difficulties.

According to a first aspect of the present invention there is provided a back-drivable robot head including:
(a) a manually-graspable driving member;
(b) a force sensor for sensing forces applied to the driving member by a user
(c) an arm for carrying a tool the position of which is to be controlled; and
(d) a first rotation control mechanism for rotating the arm about a first axis in response to the sensed forces;
characterised in that the first rotation control mechanism comprises a first rotational motor coupled to a first lead screw; and a bearing which moves longitudinally of the first lead screw as it rotates, the bearing being pivotally coupled to an offset crank of or secured to the arm.

According to a second aspect of the present invention there is provided a back-drivable robot head including:
(a) a manually-graspable driving member;
(b) a force sensor for sensing forces applied to the driving member by a user
(c) an arm for carrying a tool the position of which is to be controlled; and
(d) a first rotation control mechanism for rotating the arm about a first axis in response to the sensed forces;
characterised in that the first rotation control mechanism comprises a first rotational motor, an output of which is converted first to longitudinal motion and then back to rotational motion of the arm.

According to a third aspect of the present invention there is provided a back-drivable robot head including:
(a) a manually-graspable driving member,
(b) a force sensor for sensing forces applied to the driving member by a user
(c) an arm for carrying a tool the position of which is to be controlled; and
(d) a first rotation control mechanism for rotating the arm about a first axis in response to the sensed forces;
characterised in that the first rotation control mechanism comprises a first rotational motor, an output of which is converted first to longitudinal motion and then back to rotational motion of the arm; the head further including a first input encoder for measuring rotation of the first motor, a first output encoder for measuring the angular position of the arm about the first axis, and in which the measurement from the first output position encoder is compared with an expected arm position based on the measurement from the first input position encoder, an alarm being raised if the expected position is inconsistent with the actual position.

BRIEF DESCRIPTION OF THE DRAWINGS

The invention may be carried into practice in a number of ways, and one specific embodiment will now be described, by way of example, with reference to the accompanying drawings, in which.

DETAILED DESCRIPTION OF THE INVENTION

Figure 1:
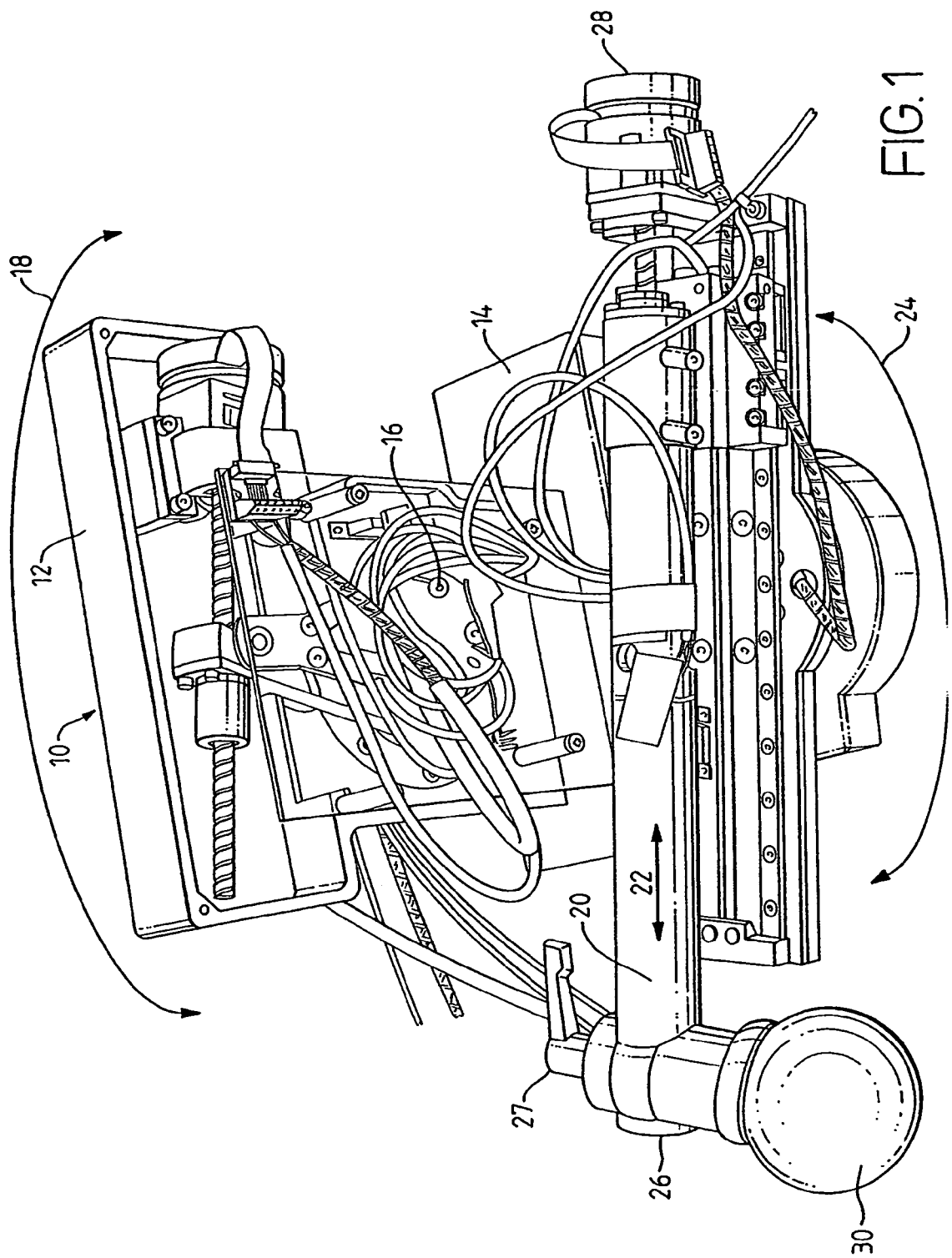
FIG. 1 is a schematic view of a preferred surgical robot head, with the covers removed.
Figure 2:
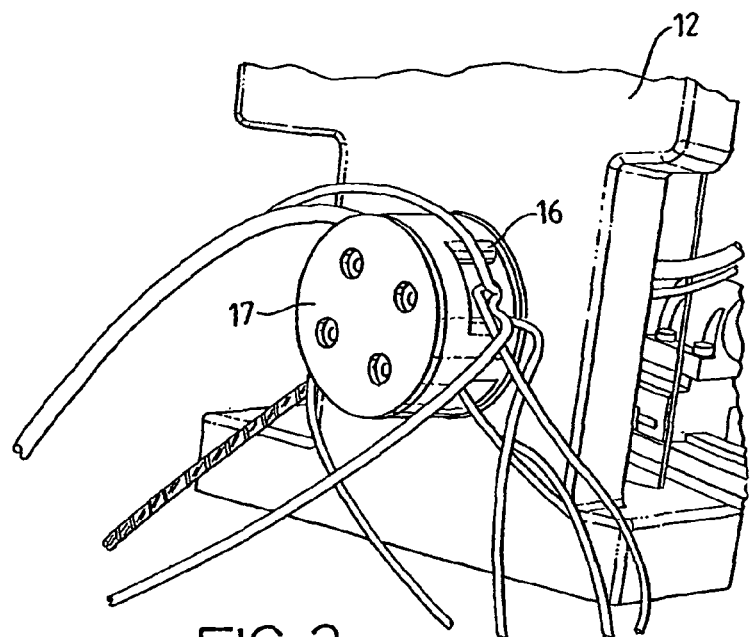
FIG. 2 shows the rear mounting, for mounting the head onto a gross positioning device.

FIG. 1 shows a surgical robot head in accordance with a preferred embodiment of the invention. The head consists of a generally L-shaped frame 10 having an upper portion 12 and a lower portion 14. The upper portion 12 has a rotatable mounting 16, best shown in FIG. 2, having a rear mounting plate 17 which allows the head to be bolted to a static gross positioning device (not shown). Once so mounted, the whole of the robot head can then rotate about a horizontal pitch axis, as shown by the arrows 18.

Mounted to the lower portion 14 of the frame is a telescopic arm 20, capable of extending and retracting by means of a motor 28, as shown by the arrows 22. The arm is mounted for rotation about a vertical yaw axis, as shown by the arrows 24. The horizontal pitch axis and the vertical yaw axis intersect on the longitudinal axis of the arm 20.

In use, a cutter (not shown) is inserted into a bore 26 at one end of the arm, and is locked into place by means of a locking handle 27.

The surgeon operating the device grasps a handle 30, and manually guides the cutter through the bone as required. Sensors within the handle 30 or between the handle and the body detect the forces that are being applied, and adjust the pitch, yaw and in/out motions accordingly, as will be described in more detail below. It will be understood of course that in the operating theatre most of the mechanical parts displayed in FIG. 1 will be hidden behind smooth external covers; these have been omitted from FIG. 1 to expose the workings of the head.

Figure 3:
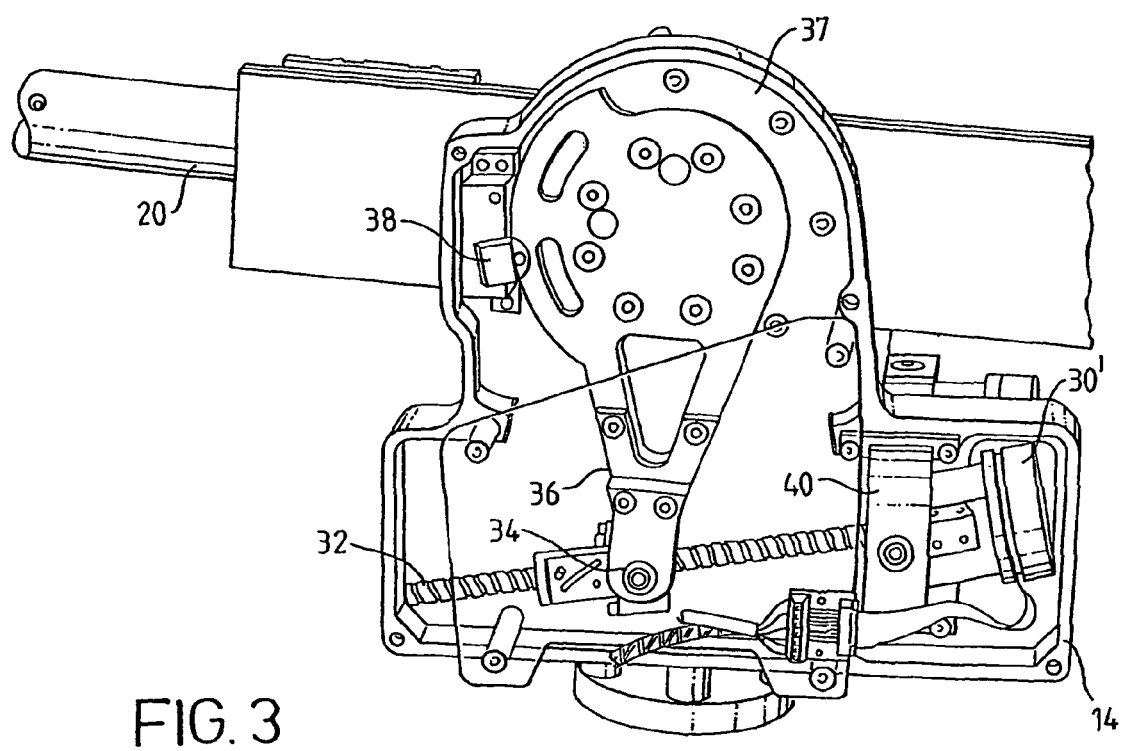
FIG. 3 is a view from below, showing rotational control of the telescopic arm about a vertical axis.

FIG. 3 is a view from below, showing the mechanism for controlling rotational movement of the arm 20 about the vertical yaw axis. Rotation of a lead screw 32 by means of a pancake or other motor 30' causes a ball screw or bearing 34 to move up and down the lead screw. The ball screw 34 is connected to an arm or crank 36 which is itself connected to the telescopic arm 20. Accordingly, the yaw position of the arm 20 is controlled by the linear position of the ball screw 34 on the lead screw 32.

The crank arm 36 connects to the lead screw 32 by means of a pivoting linkage, to allow for the different angles of the crank arm as the ball screw 34 moves along. Movement also causes the lead screw 32 to rotate slightly about a pivot bearing 40 adjacent the motor 30'.

Figure 4:
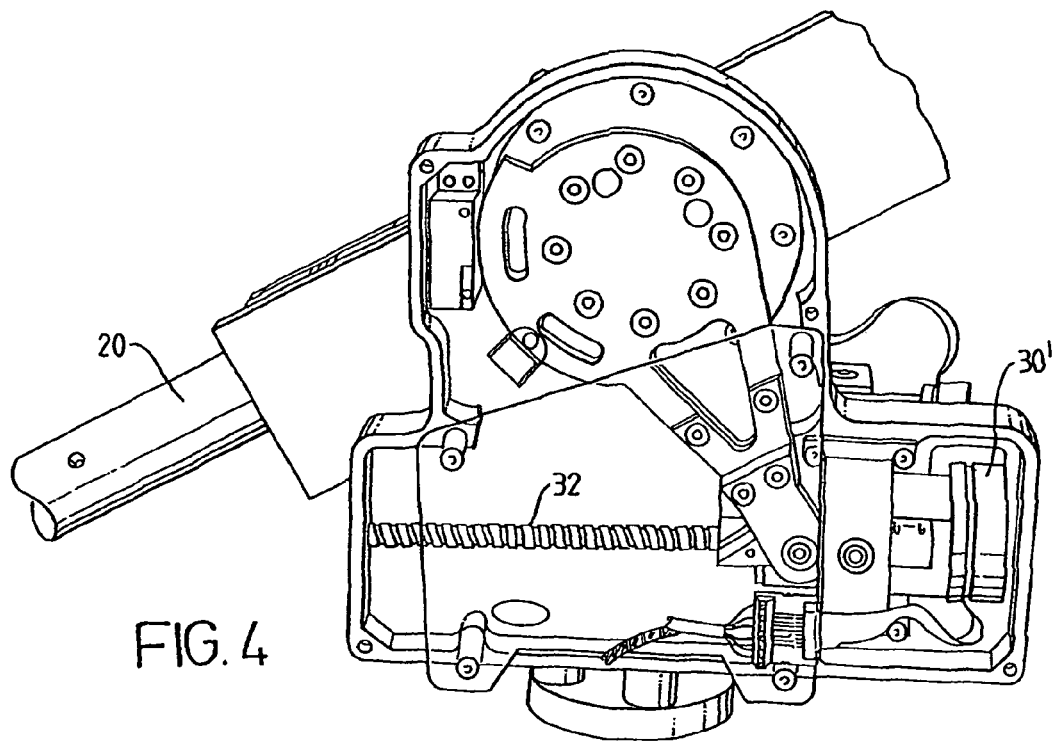
FIG. 4 shows the telescopic arm at one extreme end of its range of rotation.
Figure 5:
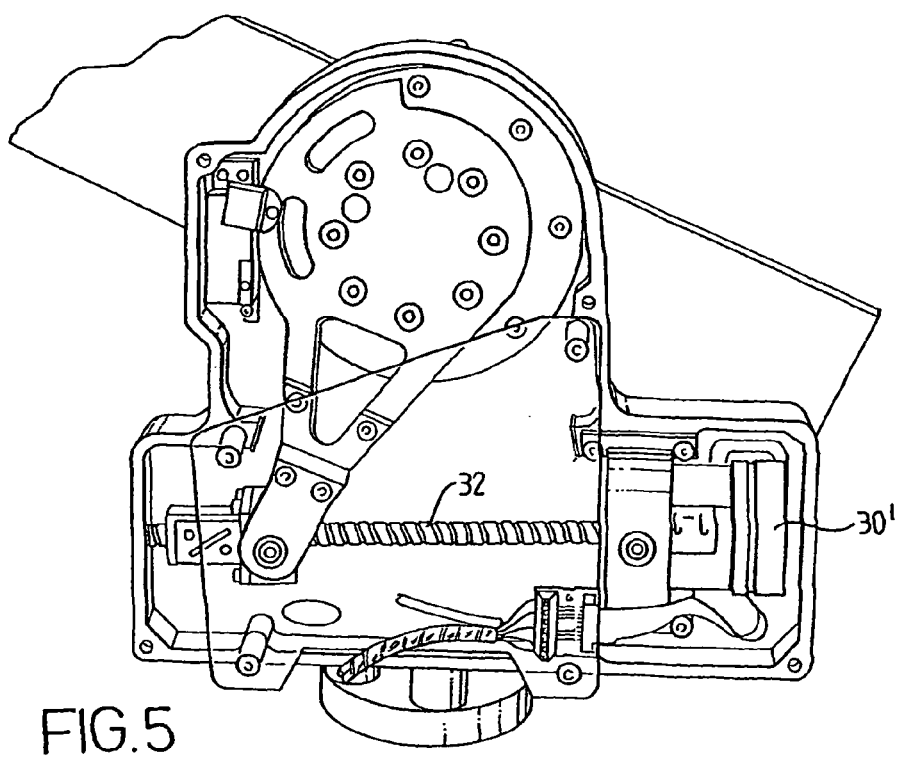
FIG. 5 shows the arm at the other extreme end of its range.

FIGS. 4 and 5 show, respectively, the arm 20 at each end of its range of movement. As may be seen, in both of these extreme positions, the lead screw 32 is substantially horizontal in the drawing; compare this with FIG. 3, in which the lead screw 32 has been pushed downwards slightly due to the length of the crank 36.

Figure 6:
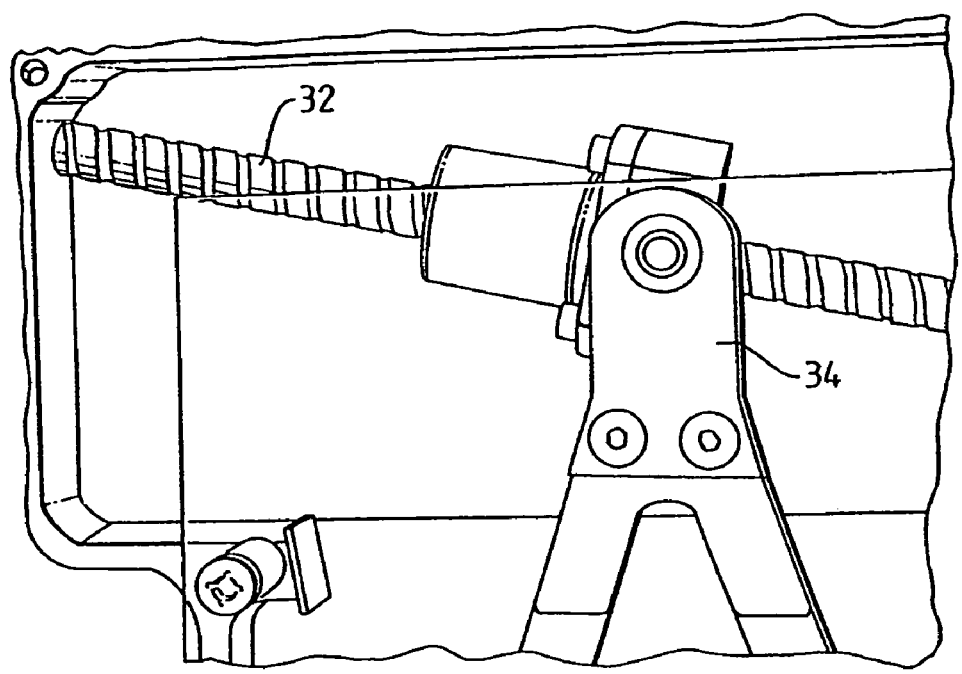
FIG. 6 shows the pivotal connection between the offset crank and the lead screw.
Figure 7:
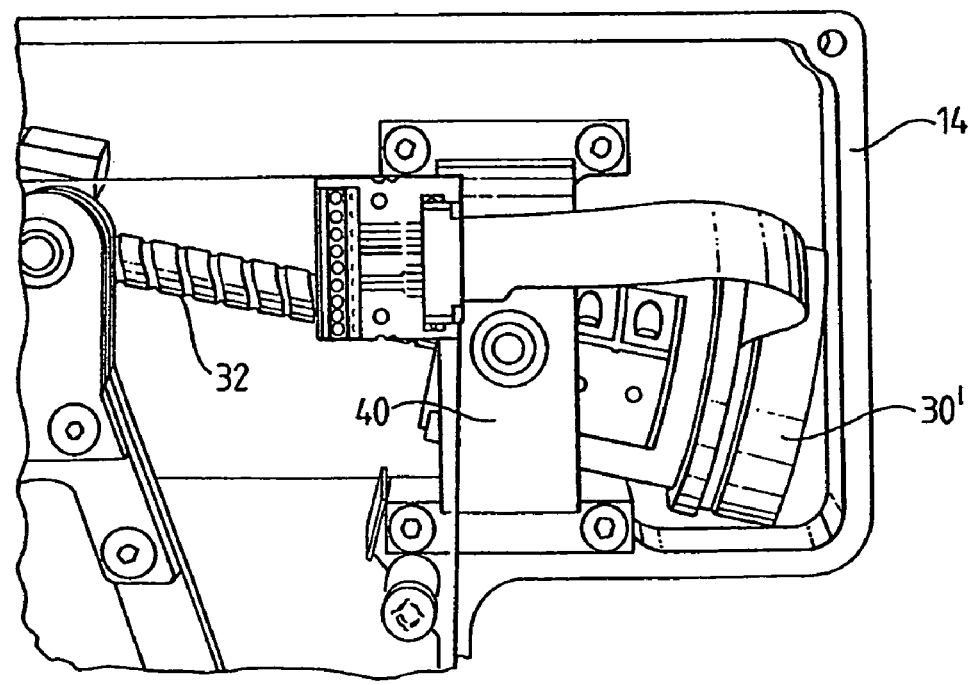
FIG. 7 shows the mounting of the motor that drives the lead screw.

FIG. 6 is a close-up view showing in more detail the pivotal coupling between the crank arm 36 and the lead screw 32. FIG. 7 is a further close-up showing the pivotal coupling of the motor 30' and the crank arm 32 with respect to the lower part 14 of the frame.

As is best seen in FIG. 6, the lead screw 32 is formed with a high lead angle: this allows for low gear ratios to be used, as well as allowing the system to be back drivable (in other words, the surgeon can simply pull the arm 20 around by grasping the handle 30 shown in FIG. 1). With the arrangement described, no gear box is required, and the motor 30' (FIG. 3) is simply attached directly to the end of the lead screw 32.

Figure 8:
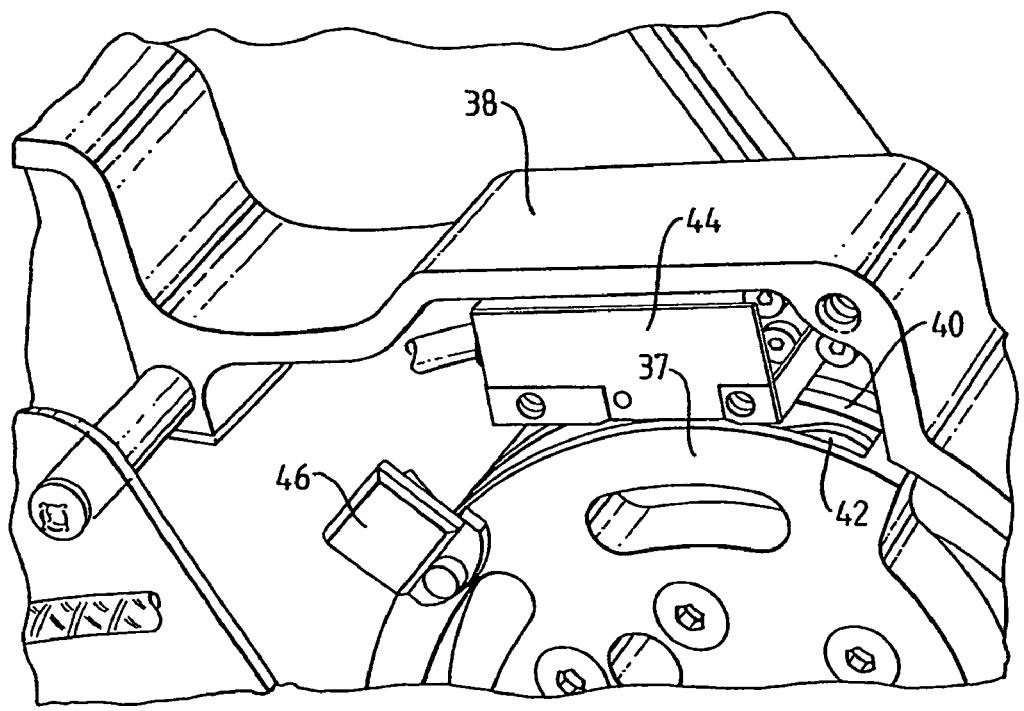
FIG. 8 shows the primary sensor which determines rotational position.

Turning back now to FIG. 3, it will be seen that surrounding the vertical yaw axis is a cylindrical structure 37. This is used in order to determine the exact rotational position of the arm 20, in conjunction with an encoder generally indicated at 38. As is best shown in FIG. 8, the cylindrical structure 37 defines a circumferential cam surface 40 onto which is secured a thin reflective strip 42. A sensor 44 picks up patterns (not shown) on the strip, from which the angular position of the arm 20 may be accurately determined. In this embodiment, a stop 46 defines a nominal zero position, with the actual position at any time simply being determined by counting the number of pulses the sensor 44 has detected as the arm moves away from the zero position. The use of a circumferential strip 42 as described substantially eliminates errors due to backlash.

In order to protect against mechanical or other fault, an additional safety sensor (not shown) is built into the motor 30'. Position signals from the motor's sensor and from the main sensor 44 are compared and, if there is any discrepancy, an alarm is raised and the power to the cutter is switched off immediately. Because of the changing angles of the crank arm 36, there is not a linear relationship between the pulses detected by the motor sensor and those detected by the main sensor 44. Accordingly, it is convenient for the comparison to be carried out in software. Suitable software will not be described here, as it is well within the capabilities of a skilled person in the field to construct a function or a mapping defining the non-linear relationship, and then setting up a comparison with appropriate trigger points for switching off the power.

Turning back to FIG. 1, it will be seen that the mechanism for controlling rotation of the head about the horizontal pitch axis, on the mount 16, is virtually identical to the mechanism already described for rotation about the vertical yaw axis. The mechanisms within the upper part 12 of the frame 10, and surrounding the mount 16, will not therefore be described separately.

Figure 9:
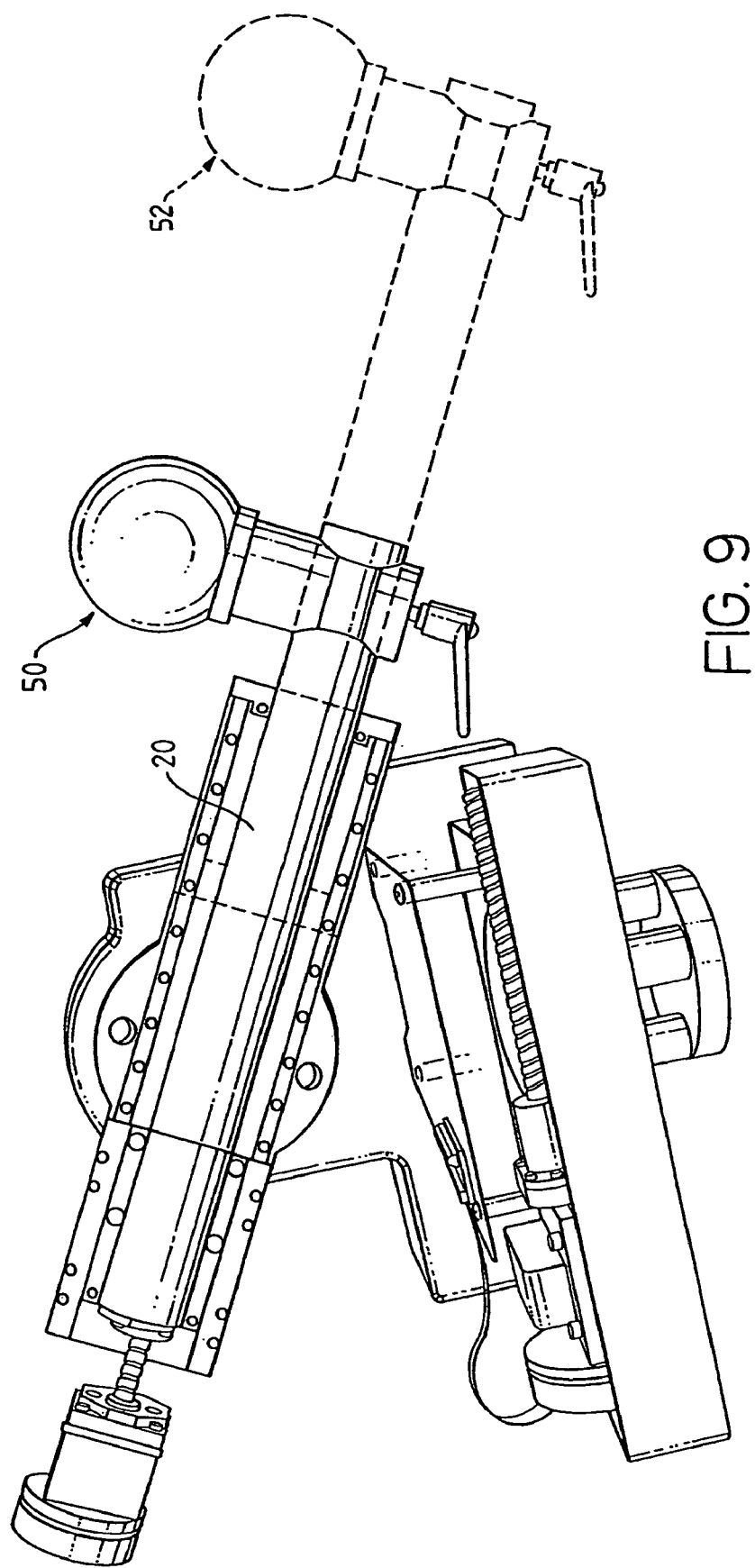
FIG. 9 shows the telescopic arm at the two extreme limits of its range.

FIG. 9 shows the arm 20 in its retracted position 50 and in an extended position 52. Extension is effected by means of the motor 28 (FIG. 1) which turns a lead screw 54. Unlike the motors for the yaw/pitch actions, this motor is fixed in position. As the motor rotates and the screw turns, a barrel portion 56 of the arm, mounted to a carriage, is moved along the guide tracks 58.

Figure 10:
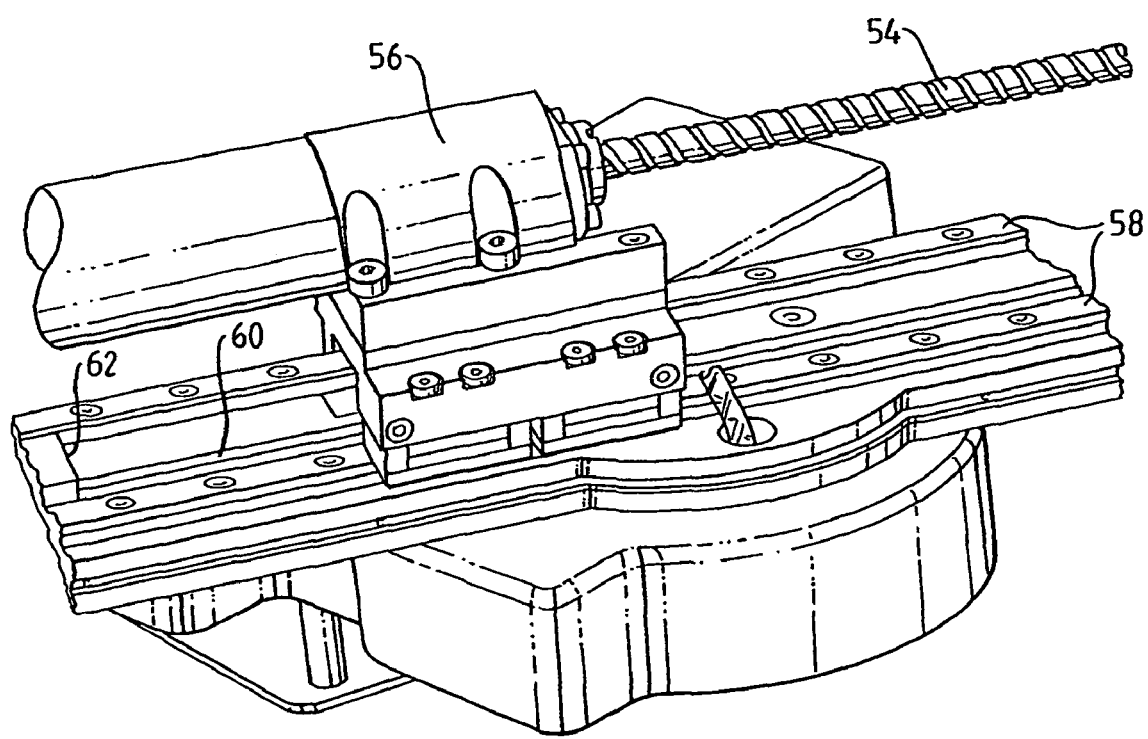
FIG. 10 shows the tracks on which the telescopic arm moves.

Between the rails 58 is a positioning strip 60. The position of the carriage with respect to this strip is sensed by means of a position sensor (not visible in the drawings) positioned beneath the barrel 56. Just visible at the left hand edge of FIG. 10 is a carriage stop which acts as a zero-point indicator. The exact location of the carriage along the rails 50 is determined by the number of pulses received by the sensor from corresponding markings on the strip as the carriage moves away from the zero point.

For additional security, a secondary sensor (not shown) is provided in association with the motor 28. A hardware or software comparison is made between the measured position of the barrel 56 as determined by the main sensor, and the position as determined by the secondary sensor. If the sensors do not agree, an alarm is raised and power to the cutter is immediately switched off.

The manually-graspable knob 30, best seen in FIG. 1, has a force sensor (not shown) mounted within it, along with associated wiring and electronics. The outer part of the knob is connected to the sensor which is itself connected to the arm 20. Hence, any force the surgeon applies to the knob 30, in any direction, will automatically be sensed by the sensor. The sensor generates control signals based upon the sensed forces which are used, along with details of the current head position and cutter constraints, to control the pitch and yaw motors 30', along with the arm extension motor 28. The motors are controlled so that the surgeon feels an increasing resistance as he pushes towards a constraint boundary, and decreasing resistance as he moves away. In an unconstrained region, the motors are controlled to give an equal low resistance to movement in any direction. For the present purpose, an unconstrained region means either:

(a) when the constraints are switched off (e.g. during registration), or
(b) far away from any boundary, inside the constraint region.

When the surgeon needs to cut bone, an appropriate cutter is pushed into the bore 26, and locked in place by the locking handle 27 (FIG. 1). Alternatively, other surgical or medical instruments may be placed within the bore 26, depending upon the application.

The robot head described may also be used in non-surgical applications.

The invention claimed is:

1. A back-drivable surgical robot head comprising:
   a frame;
   an arm for carrying a tool the position of which is to be controlled;
   a manually-graspable driving member on said arm; and
   a first rotation control mechanism for rotating the arm about a first axis with respect to said frame, said first rotation control mechanism comprising:
      a first lead screw having a rotational motor coupled at one end thereof, said lead screw and motor being mounted at said one end to pivot with respect to said frame;
      a bearing which moves longitudinally of said first lead screw as it rotates, said bearing being coupled to an offset crank of or secured to said arm, said lead screw taking up a zero pivotal position when said bearing is at said one end of said lead screw, said lead screw pivoting away from the zero position as the bearing moves along said lead screw to a maximal pivotal position in which the bearing is part way along the lead screw, and returning to the zero position as the bearing reaches an extreme position at an end of the lead screw opposite said one end;
   said head being back-drivable wherein manual forces applied to said driving member by a user grasping said driving member cause said arm to rotate to a desired position, said motor responding to said manual forces to ensure that said arm moves smoothly to said position with constant low resistance in an unconstrained region and with increasing resistance towards a constraint boundary.

2. A robot head as claimed in claim 1 in which the first motor is directly secured to the first lead screw, without any intervening gears.

3. A robot head as claimed in claim 1 further including a first output position encoder for measuring the angular position of the atm about the first axis.

4. A robot head as claimed in claim 3 in which the measurement from the first output position encoder is compared with an expected arm position based on the measurement from a safety sensor, and an alarm is raised if the expected position is inconsistent with the actual position.

5. A robot head as claimed in claim 1 further including a first input position encoder for measuring rotation of the first motor.

6. A robot head as claimed in claim 1 further including a second rotation control mechanism for rotating the arm about a second axis, the said mechanism comprising a second rotational motor coupled to a second lead screw and a bearing which moves longitudinally of the second lead screw as it rotates, the bearing being pivotably coupled to an offset crank of or secured to the arm.

7. A robot head as claimed in claim 6 in which the second motor and the second lead screw are mounted for pivotal motion with respect to a frame of the head.

8. A robot head as claimed in claim 6 in which the second motor is directly secured to the second lead screw, without any intervening gears.

9. A robot head as claimed in claim 6 in which the first axis is perpendicular to the second.

10. A robot head as claimed in claim 6 in which the arm is extendible along a third axis.

11. A robot head as claimed in claim 10 in which the first, second and third axes intersect at a point.

12. A robot head as claimed in claim 10 in which the arm is extendible on a third lead screw which is rotated by a third rotational motor.

13. A robot head as claimed in claim 1 further comprising a force sensor for sensing forces applied to the driving member by a user.

14. A robot head as claimed in claim 13 wherein the first rotational control mechanism is arranged to rotate the arm about the first axis is response to the sensed forces.

* * * * *